United States Patent
Morgan

(10) Patent No.: US 6,481,888 B1
(45) Date of Patent: Nov. 19, 2002

(54) SCATTER BAN DRAPE

(76) Inventor: R. Hank Morgan, 2516 Montgomery, Santa Rosa, CA (US) 95405

( * ) Notice: Subject to any disclaimer, the term of this patent is extended or adjusted under 35 U.S.C. 154(b) by 0 days.

(21) Appl. No.: 09/416,377

(22) Filed: Oct. 12, 1999

(51) Int. Cl.$^7$ ............................................... H05G 1/00
(52) U.S. Cl. .................. 378/204; 250/515.1; 250/519.1
(58) Field of Search ............................... 378/203, 204; 250/515.1, 519.1

(56) References Cited

U.S. PATENT DOCUMENTS

| | | | | |
|---|---|---|---|---|
| 1,574,884 A | * | 3/1926 | Hendricks | 250/515.1 |
| 1,607,140 A | * | 11/1926 | Wappler | 250/515.1 |
| 2,718,598 A | | 9/1955 | Graf | 250/515.1 |
| 2,794,128 A | | 5/1957 | Shasky | 250/519.1 |
| 3,967,129 A | | 6/1976 | Winkler | 250/517.1 |
| 3,984,695 A | | 10/1976 | Collica et al. | 250/515.1 |
| 3,984,696 A | | 10/1976 | Collica et al. | 250/515.1 |
| 4,062,518 A | | 12/1977 | Stivender et al. | 250/519.1 |
| 4,581,538 A | | 4/1986 | Lenhart | 250/519.1 |
| 4,938,233 A | | 7/1990 | Orrison, Jr. | 128/849 |
| 4,957,120 A | | 9/1990 | Grier-Idris | |
| 4,991,242 A | | 2/1991 | Brown | 5/601 |
| 5,006,718 A | | 4/1991 | Lenhart | 250/519.1 |
| 5,417,225 A | | 5/1995 | Rubenstein et al. | 128/849 |
| 5,892,238 A | * | 4/1999 | Huttner et al. | 250/515.1 |

FOREIGN PATENT DOCUMENTS

| | | |
|---|---|---|
| DE | 1466848 | 3/1964 |
| DE | 2313201 | 9/1974 |
| DE | 8800284 | 3/1988 |
| DE | 19619297 | 2/1997 |
| DE | 29706321 | 6/1997 |

* cited by examiner

*Primary Examiner*—Robert H. Kim
*Assistant Examiner*—Allen C. Ho
(74) *Attorney, Agent, or Firm*—Dergosits & Noah LLP

(57) ABSTRACT

An x-ray shielding device for use with an examination table. The x-ray shielding device includes a rectangularly shaped drape positioned on the tabletop and sized to extend over the width of the top. At least a portion of the drape extending over the width is configured for connecting to and supporting x-ray shielding panels.

9 Claims, 2 Drawing Sheets

SCATTER BAN DRAPE

TECHNICAL FIELD OF THE INVENTION

The present invention relates to x-ray shielding for use with an examination table which substantially reduces x-ray radiation from contacting persons working in close proximity thereto. The present invention is particularly adapted for use with fluoroscopes having C-arms supporting x-ray emitters and collectors used during patient examination and manipulation.

BACKGROUND OF THE INVENTION

Fluoroscopes and other x-ray generating devices are used quite commonly in a variety of examination and invasive surgical procedures. Fluoroscopes have been employed to guide and to assist in manipulation of surgical instruments. To protect operating room personnel from scattered radiation, shielding is commonly employed. Oftentimes, practitioners wear lead drapes and aprons which are not entirely effective for the entire human torso is not always completely covered. For example, as surgeons and other medical practitioners perform their various operating room functions, body parts such as armpits and neck regions become particularly exposed to scattered radiation. Further, currently available surgical radiation shields are designed primarily to attenuate radiation either above or below the patient plane. Such shields provide limited protection to operating room personnel from the significant radiation sources including radiation emanating from the patient on whom the surgical procedure is being performed.

Current fluoroscope equipment used in performing surgical procedures provides primary beam collimation resulting in some x-ray tube radiation leakage. However, when x-ray radiation interacts with a patient, significant radiation is scattered through and from the patient. This scattered radiation is a leading source of exposure to attending personnel. Exposure rates in excess of 1 rem/hour have been measured.

Fluoroscopes are oftentimes configured on a C-arm whereby an emitter is located at one arm extremity which, in use, provides a beam source below the patient and the horizontally extending examination tabletop while a an image intensifier, located at the second C-arm extremity is positioned above the patient. Oftentimes, x-ray radiation emanating from the emitter scatters from the patient's torso and table and is reflected onto the floor and is absorbed by medical personnel. Prior efforts to eliminate or at least minimize such scattered radiation have proven ineffective for the geometry of the C-arm itself interferes with various x-ray shielding expedience.

In addition to the above, it is recognized that examination tables of unrelated manufacturers are of a myriad of designs. In providing an x-ray shielding device, an important consideration was the development of shielding which could be universally employed in conjunction with various and diverse table configurations eliminating the need for providing separate design embodiments for each table contemplated for use herewith.

It is thus an object of the present invention to provide an improved x-ray shielding device for use with an examination table while eliminating the various limitations discussed above inherent in the prior art.

These and further objects will be more readily apparent when considering the following disclosure and appended claims.

SUMMARY OF THE INVENTION

An x-ray shielding device for use with an examination table, the table having a substantially horizontal top for supporting a patient. The top is further characterized as being substantially rectangular in shape having two substantially parallel long edges extending a length to support the entire height of the patient while having two substantially parallel short edges extending to support the entire width of the patient. The examination table further comprises a pedestal supported by a base and a substantially rectangular frame located atop the pedestal for supporting the top.

The x-ray shielding device comprises a substantially rectangularly shaped drape positioned on the examination tabletop and sized to extend over the width of the top. At least a portion of the drape extending over the width of the top is provided with means for connecting x-ray shielding panels thereto. The x-ray shielding panels are removably attachable to the drape and, once in place, vertically extend from the top down towards the examination table base.

DETAILED DESCRIPTION OF THE INVENTION

Figure 1:
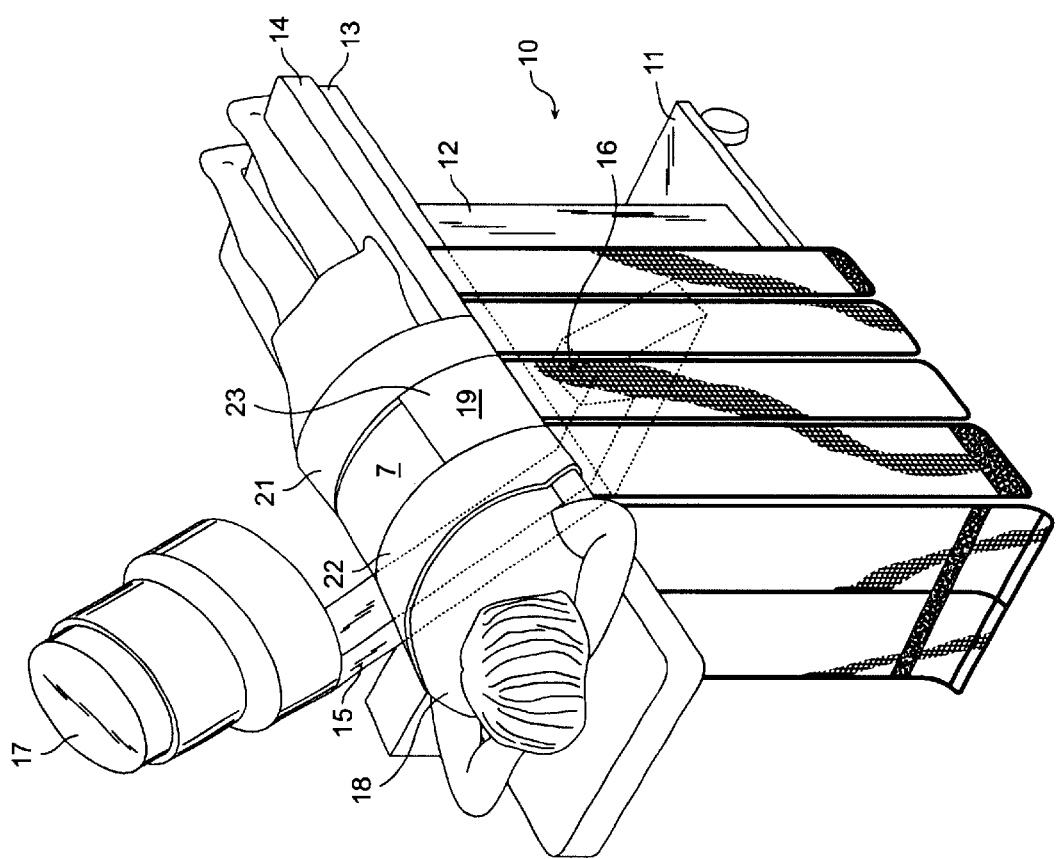
FIG. 1 is a perspective view of an examination table supporting a patient showing the installation of the x-ray shielding device of the present invention.
Figure 2:
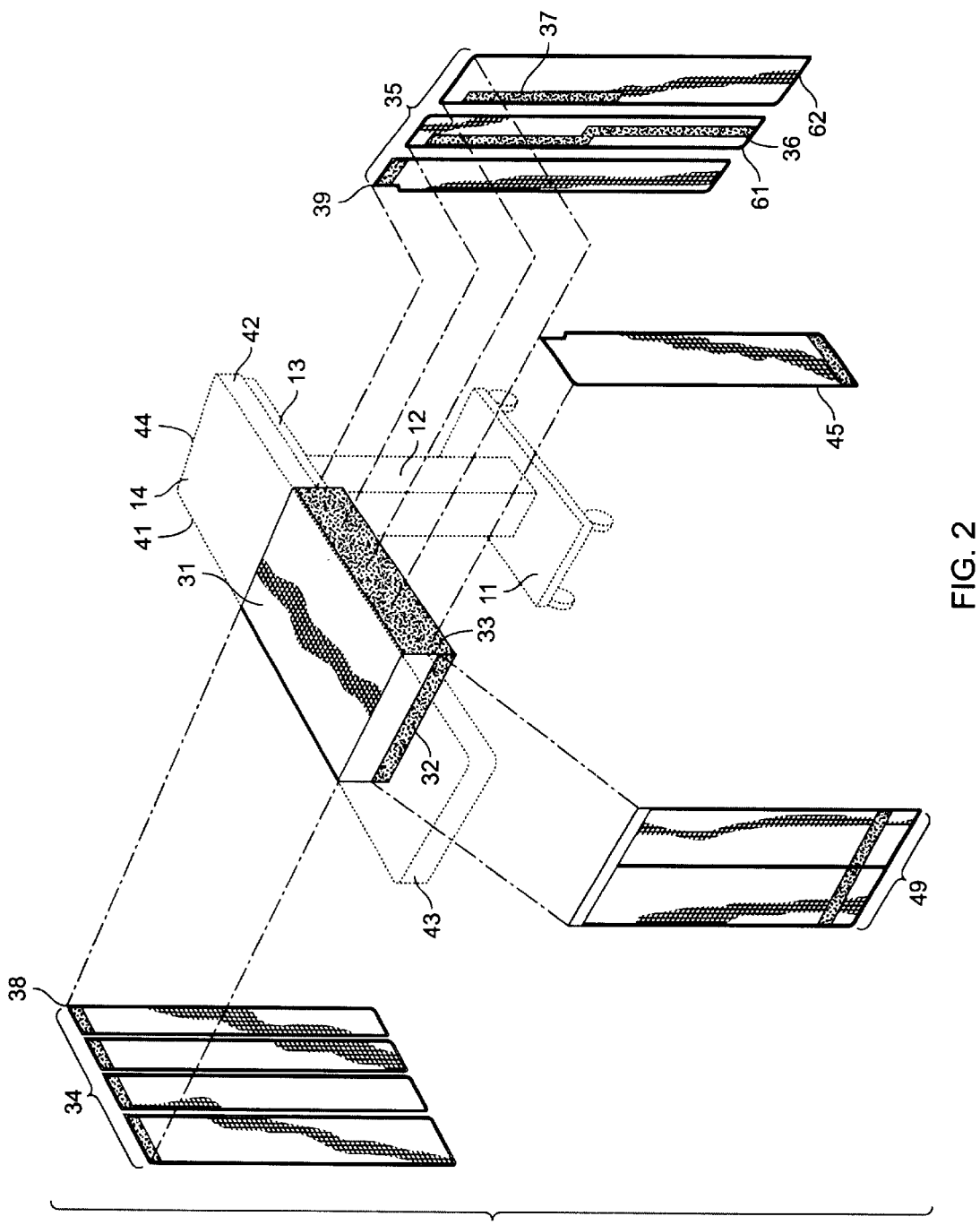
FIG. 2 is a perspective exploded view of the x-ray shielding device of the present invention.

As noted previously, the present invention deals with an x-ray shielding device for use with an examination table. Turning first to FIG. 1, examination table 10 is shown as being provided with base 11 and pedestal 12 which, in turn, supports a frame 13. Frame 13 supports tabletop 14 which is maintained on frame 13 through the use of clampings blocks described in applicant's co-pending U.S. Application No. 09/164,821 entitled PATIENT SUPPORT TABLE, the disclosure of which is incorporated by reference. As noted, examination tabletop 14 extends beyond the longitudinal dimension of frame 13 as best shown in FIG. 2.

Examination tabletop 14 is x-ray permeable and is horizontally oriented between fluoroscope emitter 16 and image intensifier 17. As shown, table 10 is configured as having a fairly expansive open area beneath frame 13 allowing for C-arm 15 of the fluoroscope to freely pass in conjunction with examination table 10 allowing for a variety of orientations facilitating the use of this device to guide surgical procedures and in performing other patient-related functions. However, as noted previously, the use of this device is hazardous to operating room personnel who must be shielded against x-rays which may leak from the fluoroscope or scatter from the air or from the patient or from reflective surfaces in the vicinity of the patient.

Referring once again to FIG. 1, fluoroscope emitter 16 is angled and positioned to expose area 9 of patient 18. To reduce x-ray reflection, the patient is provided with x-ray impermeable draping 19 in the form of strips 21 and 22 and side panel 23. Use of draping 19 further reduces risk to personnel for the area of x-ray exposure is limited to area 9 as shown.

Notwithstanding the use of protective panel 19, x-rays emanating from emitter 16 oftentimes reflect from the patient's torso and from the examination table itself. The present invention is intended to substantially reduce such exposure in the form of an expedient which can be employed in virtually any examination table currently in use.

The present invention can perhaps be best visualized by reference to FIG. 2. Examination table 10 consisting of base 11, pedestal 12 and frame 13 is employed to support substantially rectangular top 14. Top 14 is characterized as being substantially rectangular in shape having two substantially parallel long edges 41 and 42 extending a length to support the entire height of patient 18 while having two substantially parallel short edges 43 and 44 extending to support the entire width of patient 18.

In providing table 10 with the x-ray shielding device of the present invention, substantially rectangularly shaped drape 31 composed of an x-ray permeable fabric is positioned and sized to extend over the width of top 14 so that at least a portion of drape 31 extends over the sides of top 14 as shown. As such, Velcro hook and loop strips 33 extend vertically over the sides 41 and 42 for attachment to various x-ray shielding panels as discussed below.

Various x-ray shielding panels 34, 35 and 45 can be appended to drape 31 by employing attachment means such as Velcro hook and loop strips 38 and 39 for attachment to connector strip 33 and its parallel strip (not shown). Although Velcro hook and loop connection strips are the most ideal expedient for attaching x-ray shielding panels to drape 31, other attachment means such as grommets, zippers and snaps can be employed as well.

X-ray shielding panel 34, 35, 49 and 45 can be composed of, for example, lead-vinyl sheeting available from a number of manufacturers as well as panels of lead encased in suitable vinyl fabric. Each x-ray shielding panel 34, 35 and 45 is intended to drape along longitudinally extending edges 41 and 42 so that fluoroscope C-arm 15 can pass between slits created by adjacent panels as needed. As such, the present invention provides a typical examination table with great flexibility in enabling the C-arm to be positioned anywhere along the longitudinal edge of the examination table while substantially preventing scattered x-ray radiation reflecting from the patient, table and floor thus impacting support personnel.

In addition to providing Velcro strips 38 and 39, panels can be customized in a number of ways. For example, Velcro hook and loop strips 37 can be provided in adjacent panels so that when the panels are configured as shown in FIG. 2, they simply hang next to one another, freely creating the above-noted slits. However, when either panel 61 or 62 is inverted, Velcro hook and loop strips 36 and 37 assume a more proximate orientation with respect to each other enabling panels to be releasably attached to one another as needed.

To further reduce the unwanted reflection of scattered x-rays, panels 41 can further be hung blocking x-ray reflection from a third side of the examination table. As a preferred embodiment, Velcro hook and loop belt 32 can be attached to frame 13 beneath tabletop 14 for releasable attachment to corresponding attachment means on panel 49.

It is noted that by practicing the present invention, virtually any examination table can be made safer by reducing the amount of scattered x-ray radiation in the vicinity of the table. Drape 31 can be sized to saddle examination tabletops 14 of virtually any width noting that no special attachment apparatus is required to support drape 31. The various x-ray shielding panels are then appended to drape 31, again not requiring any specific table configuration as support. The x-ray shielding panels can be provided in a multiple of widths and lengths noting that it is ideally intended that the shielding panels be provided of sufficient length to extend from attachment strip 33 to the floor upon which the table resides.

While the invention has now been disclosed with reference to certain preferred embodiments and exemplified with regard thereto, those skilled in the art will appreciate that various substitutions, modifications, omissions and changes may be made without departing from the spirit thereof. Accordingly, it is intended that the scope of the present invention be limited solely by the broadest interpretation accorded the appended claims.

I claim:

1. An x-ray shielding device for use with an examination table, said table having a substantially horizontal top for supporting a patient, said top being substantially rectangular in shape having two substantially parallel long edges extending a length to support the entire height of the patient and having two substantially parallel short edges extending a width to support the entire width of the patient, said examination table further comprising a pedestal supported by a base and a substantially rectangular frame located atop said pedestal for supporting said top, said x-ray shielding device comprising a substantially rectangularly shaped drape positioned on said top and sized to extend over said width of said top, at least that portion of said drape extending over said width having means for connecting x-ray shielding panels thereto and x-ray shielding panels being removeably attachable to said drape and vertically extending from said top when attached to said drape.

2. The x-ray shielding device of claim 1 wherein said x-ray shielding panels are removeably attachable to said drape by use of a hook and loop straps.

3. The x-ray shielding device of claim 1 whereby a plurality of said x-ray shielding panels are attachable to said drape along at least a portion of each of said two substantially parallel long edges.

4. The x-ray shielding device of claim 3 wherein slits are formed between said plurality of x-ray shielding panels through which a portion of a C-arm of a fluoroscope can pass during patient examination.

5. The x-ray shielding device of claim 1 wherein an attachment belt is further positioned on said frame for releasable attaching x-ray shielding panels thereto.

6. The x-ray shielding device of claim 5 wherein said attachment belt is positioned on said frame substantially parallel to said substantially parallel short edges for attaching said x-ray shielding panels substantially parallel to said short edges.

7. The x-ray shielding device of claim 5 wherein said attachment belt reliably attaches to said x-ray shielding panels by the use of hook and loop strips.

8. The x-ray shielding device of claim 1 wherein said x-ray shielding panels are removeably joined to one another.

9. The x-ray shielding device of claim 1 further comprising x-ray shielding strips selectively applied to a patient's torso in areas proximate a target area through which x-rays pass.

* * * * *